(12) United States Patent
Bradford et al.

(10) Patent No.: US 12,616,798 B2
(45) Date of Patent: May 5, 2026

(54) DRUG DELIVERY DEVICE

(71) Applicant: Sanofi, Paris (FR)

(72) Inventors: Jim Bradford, Cambridgeshire (GB); Thomas Mark Kemp, Cambridgeshire (GB); William Timmis, Cambridgeshire (GB); Andrew Labat-Rochecouste, Cambridgeshire (GB); Hugo Revellat, Cambridgeshire (GB)

(73) Assignee: Sanofi, Paris (FR)

( * ) Notice: Subject to any disclaimer, the term of this patent is extended or adjusted under 35 U.S.C. 154(b) by 258 days.

(21) Appl. No.: 18/157,696

(22) Filed: Jan. 20, 2023

(65) Prior Publication Data

US 2023/0158250 A1      May 25, 2023

Related U.S. Application Data

(63) Continuation of application No. 16/758,781, filed as application No. PCT/EP2018/079918 on Nov. 1, 2018, now Pat. No. 11,583,636.

(30) Foreign Application Priority Data

Nov. 3, 2017    (EP) ...................................... 17306523

(51) Int. Cl.
A61M 5/315        (2006.01)
A61M 5/20         (2006.01)
(52) U.S. Cl.
CPC ...... A61M 5/31585 (2013.01); A61M 5/2033 (2013.01); A61M 5/31501 (2013.01); *A61M 2005/206* (2013.01); *A61M 2205/581* (2013.01)
(58) Field of Classification Search
CPC .......... A61M 5/31585; A61M 5/31501; A61M 5/2033; A61M 2005/206; A61M 2205/581
(Continued)

(56) References Cited

U.S. PATENT DOCUMENTS 11,583,636 B2 *    2/2023    Bradford ........... A61M 5/31586
2013/0324924 A1    12/2013    Brereton et al.
(Continued)

FOREIGN PATENT DOCUMENTS

CN        101119761        8/2010
CN        105517599        4/2016
(Continued)

OTHER PUBLICATIONS

International Preliminary Report on Patentability in International Application No. PCT/EP2018/079918, dated May 5, 2020, 8 pages.
(Continued)

*Primary Examiner* — Laura A Bouchelle
(74) *Attorney, Agent, or Firm* — Fish & Richardson P.C.

(57)        ABSTRACT

A drug delivery device comprises a housing adapted to receive a medicament container, a plunger and a plunger release mechanism that comprises a first plunger boss arranged on the plunger, a profiled slot arranged on the housing and adapted to be engaged by the first plunger boss so as to inhibit movement of the plunger in a distal direction. The plunger is rotatable about a longitudinal axis to release the first plunger boss from the profiled slot so as to allow movement of the plunger in the distal direction. A sleeve is coupled to the housing to permit movement of the sleeve relative to the housing. A sleeve ramp is arranged on the sleeve and adapted to engage a rib or boss on the plunger to rotate the plunger to release the first plunger boss from the profiled slot when the sleeve is moved in a proximal direction.

19 Claims, 8 Drawing Sheets

(58) Field of Classification Search
USPC ......................................................... 604/134
See application file for complete search history.

(56)                  References Cited

U.S. PATENT DOCUMENTS

| | | | |
|---|---|---|---|
| 2014/0207106 A1 | 7/2014 | Bechmann et al. | |
| 2014/0257185 A1 | 9/2014 | Bechmann et al. | |
| 2015/0094687 A1* | 4/2015 | Boyd ................ | A61M 5/31595 |
| | | | 604/218 |
| 2016/0144133 A1* | 5/2016 | Kemp ................. | A61M 5/2033 |
| | | | 604/198 |
| 2017/0021103 A1 | 1/2017 | Mosebach et al. | |
| 2018/0200442 A1 | 7/2018 | Atterbury et al. | |
| 2020/0330696 A1 | 10/2020 | Bradford et al. | |

FOREIGN PATENT DOCUMENTS

| | | |
|---|---|---|
| EP | 2823841 | 1/2015 |
| JP | 2016-523672 | 8/2016 |
| WO | WO 2006/057604 | 6/2006 |
| WO | WO 2012/110574 | 8/2012 |
| WO | WO 2012/122643 | 9/2012 |
| WO | WO 2015/004052 | 1/2015 |

OTHER PUBLICATIONS

International Search Report and Written Opinion in Application No. PCT/EP2018/079918, dated Jan. 22, 2019, 13 pages.

* cited by examiner

DRUG DELIVERY DEVICE

CROSS REFERENCE TO RELATED APPLICATIONS

The present application is a continuation of U.S. patent application Ser. No. 16/758,781, filed Apr. 23, 2020, which is the national stage entry of International Patent Application No. PCT/EP2018/079918, filed on Nov. 1, 2018, and claims priority to Application No. EP 17306523.6, filed on Nov. 3, 2017, the disclosures of which are incorporated herein by reference.

TECHNICAL FIELD

The disclosure generally relates to a drug delivery device having a plunger release mechanism.

BACKGROUND

Drug delivery devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

Plunger release mechanisms are applied to control motion of a plunger in a drug delivery device in a manner keeping the plunger in a defined position until a condition is met suddenly allowing the plunger to move within the drug delivery device thus delivering a dose of a drug from a syringe.

SUMMARY

The present disclosure provides a drug delivery device with an improved plunger release mechanism as well as a method for assembling a drug delivery device.

According to the present disclosure, a drug delivery device comprises a housing adapted to receive a medicament container, a plunger and a plunger release mechanism comprising: a first plunger boss arranged on the plunger, a profiled slot arranged on the housing and adapted to be engaged by the first plunger boss so as to inhibit movement of the plunger in a distal direction, wherein the plunger is rotatable about a longitudinal axis to release the first plunger boss from the profiled slot so as to allow movement of the plunger in the distal direction, a sleeve coupled to the housing to permit movement of the sleeve relative to the housing, wherein a sleeve ramp is arranged on the sleeve, the sleeve ramp adapted to engage a projection such as a rib or boss on the plunger to rotate the plunger to release the first plunger boss from the profiled slot when the sleeve is moved in a proximal direction.

In an exemplary embodiment, the profiled slot is adapted to induce a torque to the plunger when an axial force is applied to the plunger, wherein the profiled slot comprises at least one angled surface adapted to engage the first plunger boss to induce a torque in a first rotational direction to the plunger to release the first plunger boss from the profiled slot.

In an exemplary embodiment, the profiled slot further comprises a wall for limiting movement of the first plunger boss in the first rotational direction when engaged to the first angled surface and a second angled surface adjacent the wall and adapted to induce a torque in the first rotational direction to the plunger to release the first plunger boss from the profiled slot.

This allows for preventing the plunger from being released while the first plunger boss is engaged to the first angled surface and the wall. This state is particularly useful for storing and transporting a drug delivery device or a part thereof comprising the plunger and optionally a drive spring so that the drive spring cannot inadvertently advance the plunger, e.g. if the drug delivery device or the part thereof comprising the plunger is dropped. In order to transition the plunger into a state in which it may be released, the plunger may be moved away from the first angled surface along the wall and rotated so that the first plunger boss engages the second angled surface. The transition into this state may be performed during final assembly of a drug delivery device. If the plunger is not otherwise prevented from rotating further, the first plunger boss may slide down the second angled surface until disengaging it, allowing the plunger to advance, e.g. for displacing a medicament from a medicament container, in particular a syringe. In an exemplary embodiment, the plunger may be prevented from rotating further by a sleeve rib on a sleeve which may be moved on contact with an injection site to allow further rotation of the plunger.

In an exemplary embodiment, the drug delivery device may comprise the above described profiled slot with the first and second angled surfaces and the wall without having a sleeve ramp adapted to engage a projection such as a rib or boss on the plunger.

In an exemplary embodiment, the first angled surface and/or the second angled surface have/has an angle in a range from 30° to 70° relative to a perpendicular on a longitudinal axis of the plunger.

In an exemplary embodiment, the plunger release mechanism further comprises a second plunger boss arranged on the plunger and a sleeve rib arranged on the sleeve, the sleeve rib having a longitudinal face adapted to engage the second plunger boss preventing rotation of the plunger in the first rotational direction to keep the first plunger boss engaged to the angled surface, wherein the sleeve rib is adapted to disengage the second plunger boss when the sleeve rib is moved in a proximal direction thereby allowing the plunger to rotate in the first rotational direction and the first plunger boss to disengage the second angled surface.

In an exemplary embodiment, the plunger release mechanism further comprises an angled plunger rib on the plunger adapted to abut the sleeve rib so as to induce a torque to the plunger in the first rotational direction and push the plunger in the proximal direction when the first plunger boss is engaged to the first angled surface and to the wall.

In an exemplary embodiment, the sleeve rib comprises a distal face adapted to engage the second plunger boss so as to limit movement of the sleeve rib in a distal direction relative to the plunger.

In an exemplary embodiment, the release of the first plunger boss from the first angled surface and/or from the second angled surface and/or the release of the second plunger boss from the sleeve rib provides an audible feedback.

The sleeve may be adapted to be moved in a proximal direction relative to the housing upon contact with an injection site to disengage the sleeve rib from the second plunger boss.

In an exemplary embodiment, a drive spring is arranged within the housing and adapted to bias the plunger in the distal direction for displacing a piston of a medicament container.

In an exemplary embodiment, the plunger is hollow and the drive spring is arranged within the plunger.

In an exemplary embodiment, the housing comprises a distal region and a proximal region, wherein the proximal region comprises the profiled slot.

In an exemplary embodiment, the angled plunger rib is adapted to abut the sleeve rib upon coupling of the proximal region with the plunger and the drive spring to the distal region for moving the first plunger boss from the first angled surface to the second angled surface.

In an exemplary embodiment, the drug delivery device comprises a medicament container.

In an exemplary embodiment, the medicament container contains a medicament.

According to an aspect of the present disclosure, a method for assembling a drug delivery device, comprises providing a plunger having a first plunger boss and an angled plunger rib, providing a housing having a profiled slot comprising a first angled surface adapted to engage the first plunger boss to induce a torque in a first rotational direction to the plunger, a wall for limiting movement of the first plunger boss in the first rotational direction when engaged to the first angled surface and a second angled surface adapted to induce a torque in the first rotational direction to the plunger, providing a sleeve having a sleeve rib, inserting the plunger and a drive spring into the housing, rotating the plunger by an angle in a second rotational direction to engage the first plunger boss to the first angled surface and the wall, moving the sleeve in a proximal direction so that the sleeve rib proximally abuts the angled plunger rib thereby inducing a torque to the plunger in the first rotational direction and pushing the plunger in the proximal direction so that the first plunger boss disengages from the wall and engages the second angled surface.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
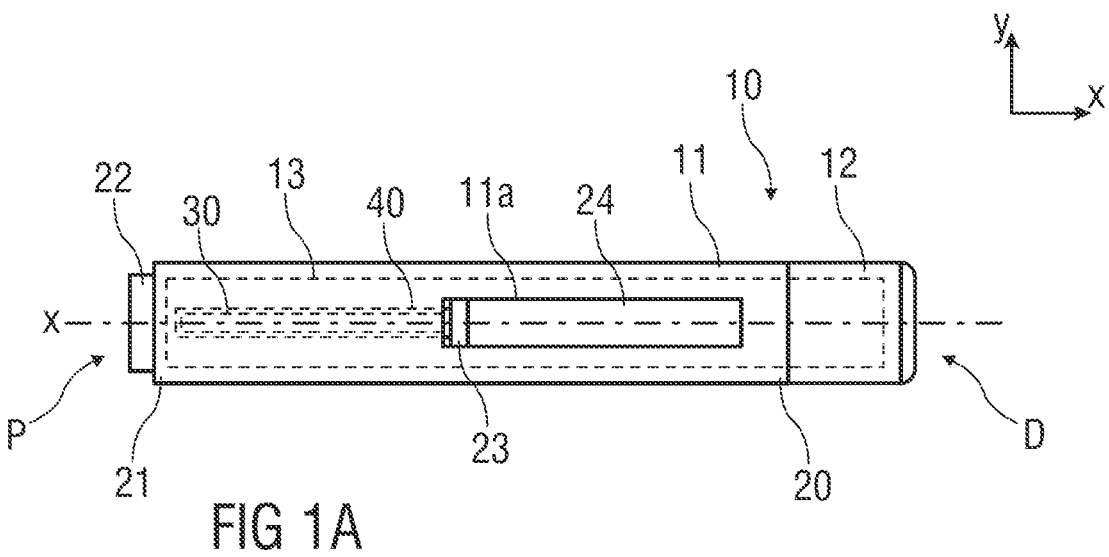
FIGS. 1A and 1B are schematic views of an exemplary embodiment of a drug delivery device.
Figure 1B:
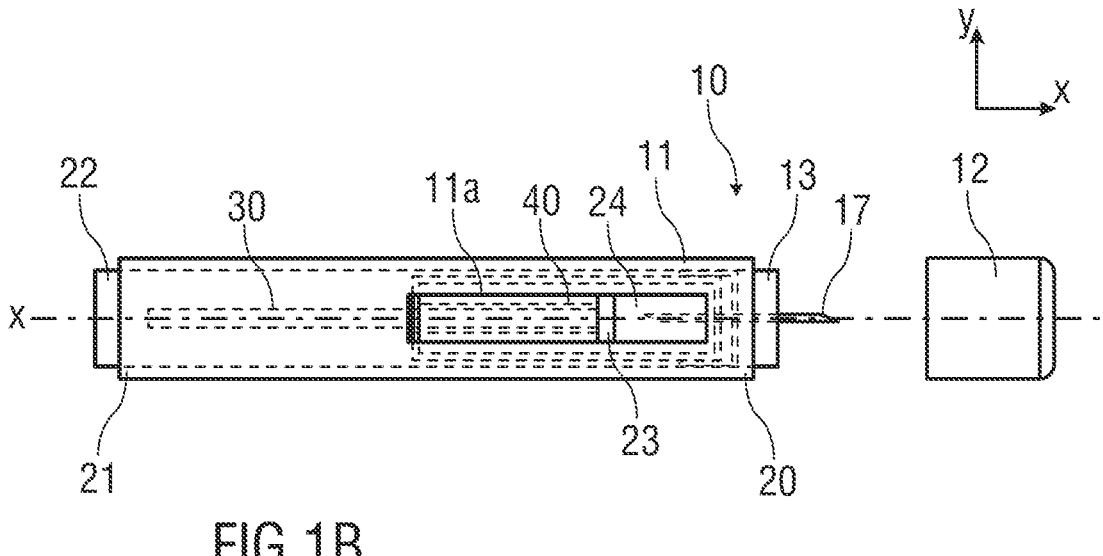

According to some embodiments of the present disclosure, an exemplary drug delivery device 10 is shown in FIGS. 1A and 1B. Device 10, as described above, is configured to inject a drug or medicament into a patient's body.

Device 10 includes a housing 11 which typically contains a reservoir containing the medicament to be injected (e.g., a syringe 24 or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11.

Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the syringe 24 can be monitored.

The drug delivery device 10 may be divided in two subassemblies, a control subassembly and a drive subassembly 10.1. This allows for improving flexibility as to the time and location of manufacture of the subassemblies and final assembly with the syringe 24.

Figure 2:
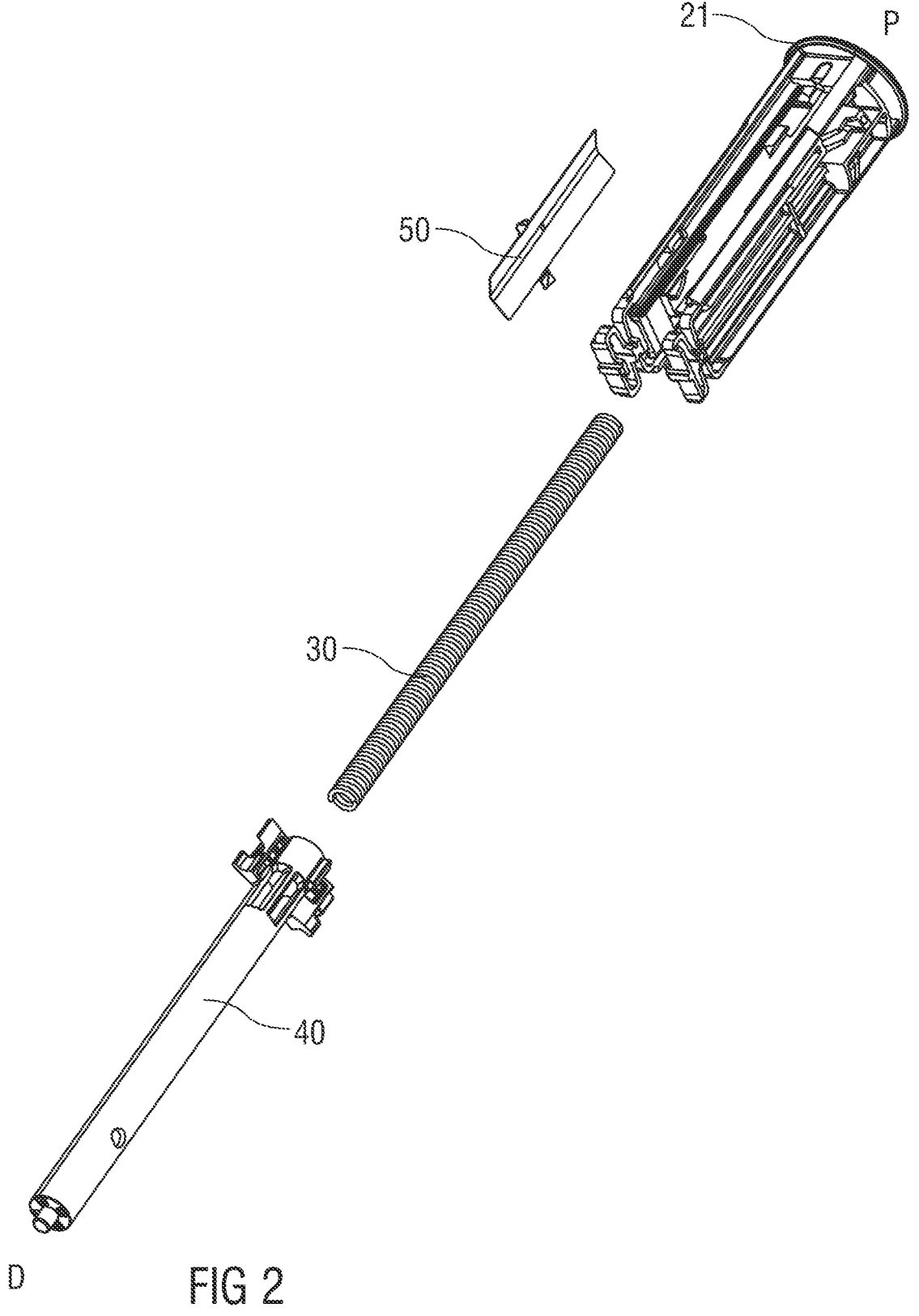
FIG. 2 is a schematic perspective exploded view of a drive subassembly of a drug delivery device.

FIG. 2 is a perspective exploded view of the drive subassembly 10.1. The drive subassembly 10.1 comprises components used to displace the medicament from the syringe 24. If the viscosity or volume of the medicament M in the syringe 24 is varied, only parts of the drive subassembly 10.1 may need to be changed. The drive subassembly 10.1 comprises the plunger 40, the drive spring 30 and the proximal region 21 of the housing 11. In an exemplary embodiment, the drive subassembly 10.1 may be assembled in a process which requires virtually only axial motion except for the plunger 40. In order to assemble the drive subassembly 10.1 the drive spring 30 is inserted into the plunger 40 and the plunger 40 is inserted in the proximal region 21 in the proximal direction P thereby compressing the drive spring 30. Once the plunger 40 reaches a compressed position it is rotated by an angle, e.g. approximately 30° to lock it to the proximal region 21. In an exemplary embodiment the proximal region 21 could have a cam surface which could induce this rotation prior to the plunger 40 reaching the compressed position.

Furthermore, a feedback element 50, e.g. a spring element may be provided to indicate an event, e.g. an end of dose, by providing an audible and/or tactile feedback.

Figure 3:
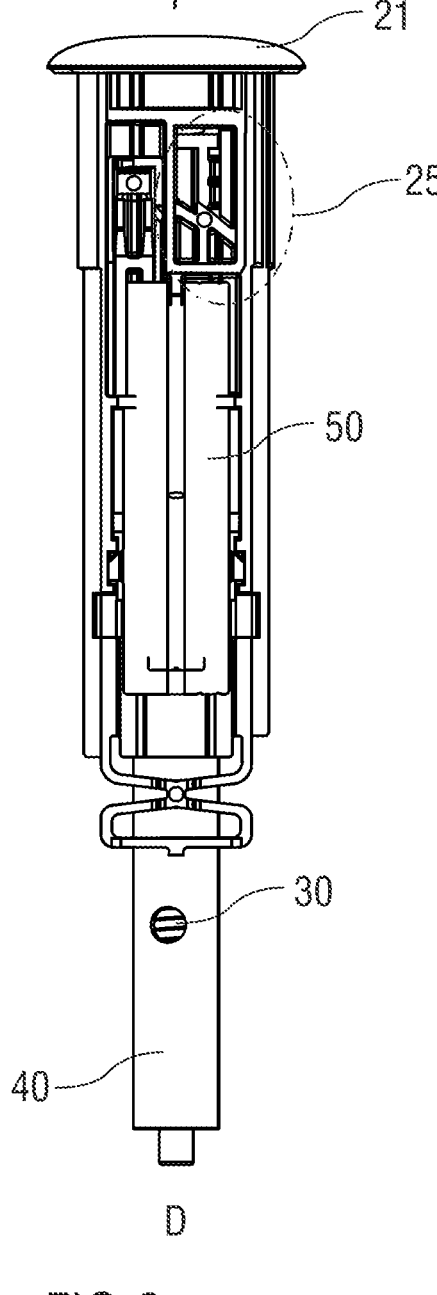
FIG. 3 is a schematic side view of the drive subassembly.
Figure 4A:
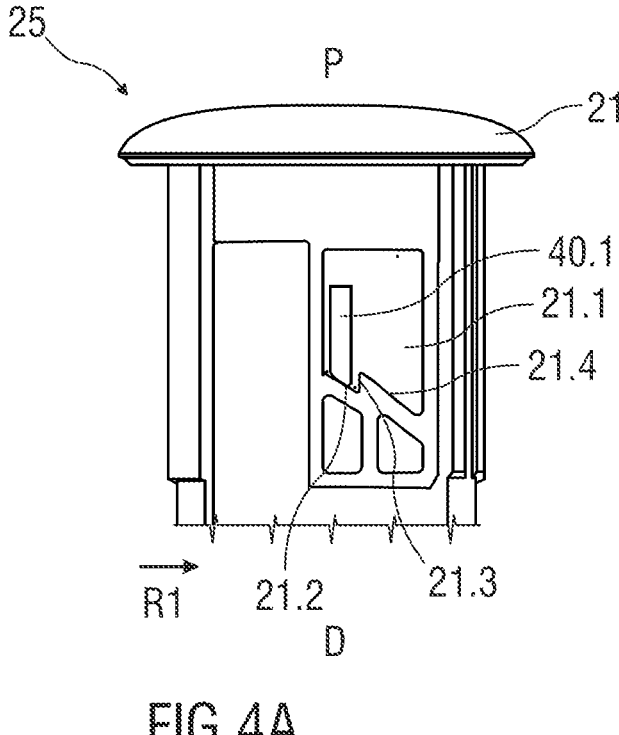
FIGS. 4A and 4B are schematic detail views of the drive subassembly showing a plunger release mechanism.
Figure 4B:
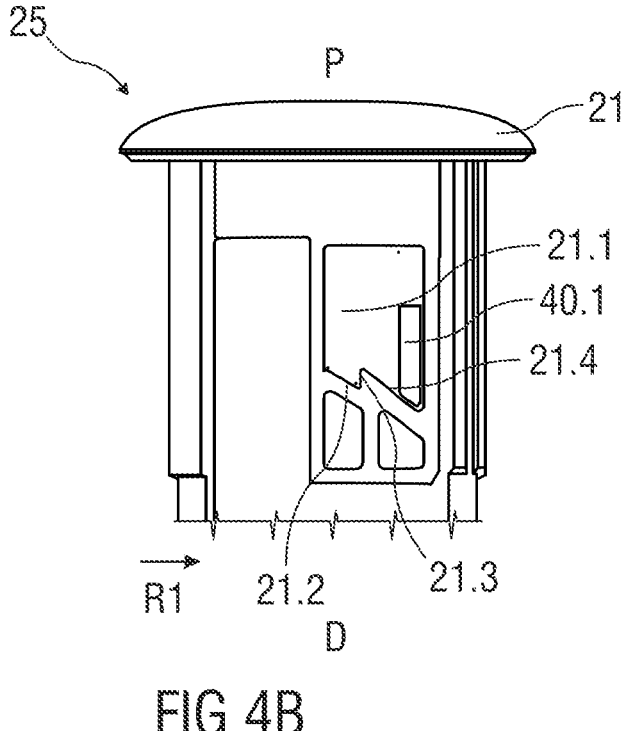

FIG. 3 is a schematic side view of the drive subassembly 10.1. FIGS. 4A and 4B are schematic detail views of the drive subassembly 10.1 showing part of a plunger release mechanism 25.

The plunger release mechanism 25 controls the activation of syringe emptying. The plunger release mechanism 25 is adapted to release the plunger 40 once the sleeve 13 is depressed and reaches a retracted position RP within the housing 11.

The plunger release mechanism 25 comprises a first plunger boss 40.1 arranged on the plunger 40 and a profiled slot 21.1 in the proximal region 21 of the housing 11. The profiled slot 21.1 comprises a first angled surface 21.2 adapted to engage the first plunger boss 40.1 to induce a torque in a first rotational direction R1 to the plunger 40, a wall 21.3 for limiting movement of the first plunger boss 40.1 in the first rotational direction R1 when engaged to the first angled surface 21.2. Furthermore, the profiled slot 21.1 comprises a second angled surface 21.4 adapted to engage the first plunger boss 40.1 to induce a torque in the first rotational direction R1 to the plunger 40.

The first angled surface 21.2 and/or the second angled surface 21.4 may have an angle in a range from 30° to 70° relative to a perpendicular on the longitudinal axis X of the drug delivery device 10 which may also be the longitudinal axis of the plunger 40.

In a first state shown in FIG. 4A, the first plunger boss 40.1 is engaged to the first angled surface 21.2. Due to the drive spring 30 acting on the plunger 40, the first plunger boss 40.1 is pressed against the first angled surface 21.2 in a distal direction D such that a torque is induced to the plunger 40 in the first rotational direction R1 so that the first plunger boss 40.1 slides along the first angled surface 21.2 until it abuts the wall 21.3 so that rotation of the plunger 40 in the first rotational direction R1 is halted.

FIG. 4B shows the plunger release mechanism 25 in a second state. Starting from the first state, the plunger 40 has been moved a distance at least as long as the wall 21.3 in the proximal direction P such that the wall 21.3 no longer limits movement of the first plunger boss 40.1 in the first rotational direction R1. The plunger 40 has then been rotated further in the first rotational direction R1 so that the first plunger boss 40.1 engages the second angled surface 21.4. Due to the drive spring 30 acting on the plunger 40, the first plunger boss 40.1 is pressed against the second angled surface 21.4 in a distal direction D such that a torque is induced to the plunger 40 in the first rotational direction R1 so that the first plunger boss 40.1 slides along the second angled surface 21.4. If the plunger 40 is not otherwise prevented from rotating further, the first plunger boss 40.1 may slide down the second angled surface 21.4 until disengaging it, allowing the plunger 40 to advance in the distal direction D to displace the medicament from the syringe 24.

In an exemplary embodiment, movement of the plunger 40 from the first state in the proximal direction P and onto the second angled surface 21.4 may be achieved by the sleeve 13 interacting with the plunger 40, e.g. by engaging the first plunger boss 40.1 or a further plunger boss or rib on the plunger (not shown).

An exemplary embodiment of the plunger release mechanism 25 is shown in more detail in FIGS. 5, 6, 7 and 8.

Figure 5:
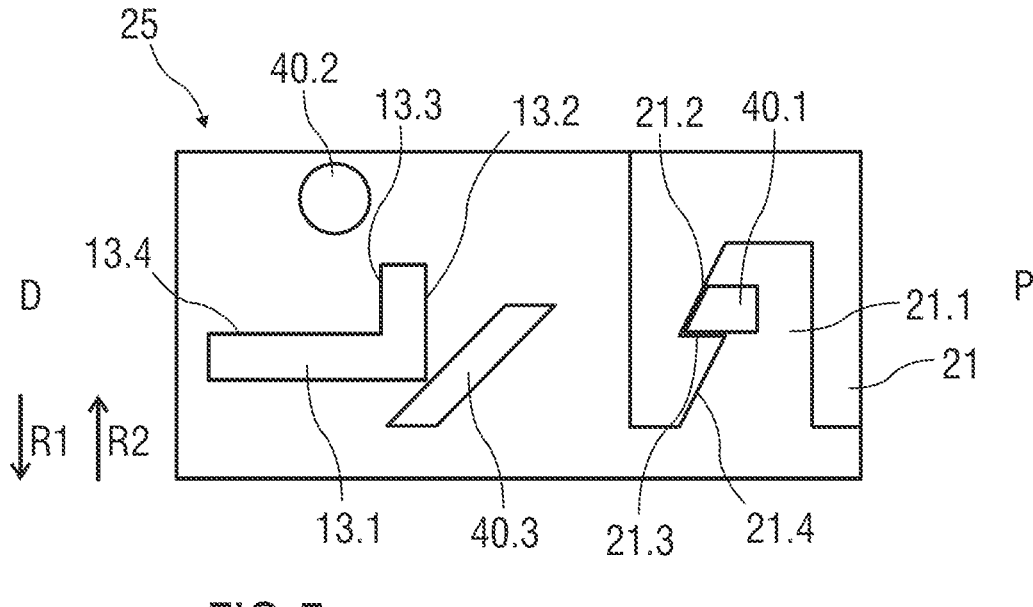
FIG. 5 is a schematic view of an exemplary embodiment of the plunger release mechanism during assembly of the drive subassembly.

FIG. 5 shows the plunger release mechanism during assembly of the drive subassembly 10.1.

The plunger release mechanism 25 is adapted to release the plunger 40 once the sleeve 13 is depressed and reaches a retracted position within the housing 11.

The plunger release mechanism 25 comprises the plunger 40, the proximal region 21, and the sleeve 13 interacting with each other. The sleeve 13 and the proximal region 21 are configured to move only in parallel with the longitudinal axis X relative to each other whereas the plunger 40 can move both in parallel with the longitudinal axis X and rotate about the longitudinal axis X. The parts of the plunger release mechanism 25 may be essentially rigid and require no deformation in order to function correctly.

The parts arranged for engaging the plunger 40, proximal region 21 and sleeve 13 comprise: a first plunger boss 40.1 on the plunger 40, a second plunger boss 40.2 on the plunger 40, an angled plunger rib 40.3 on the plunger 40, a profiled slot 21.1 in the proximal region 21 adapted to interact with the first plunger boss 40.1, a sleeve rib 13.1 on the sleeve 13 comprising a proximal face 13.2 adapted to interact with the angled plunger rib 40.3, a distal face 13.3 and a longitudinal face 13.4 adapted to interact with the second plunger boss 40.2.

The profiled slot 21.1 comprises a first angled surface 21.2 adapted to engage the first plunger boss 40.1 to induce a torque in a first rotational direction R1 to the plunger 40, a wall 21.3 for limiting movement of the first plunger boss 40.1 in the first rotational direction R1 when engaged to the first angled surface 21.2. Furthermore, the profiled slot 21.1 comprises a second angled surface 21.4 adapted to engage the first plunger boss 40.1 to induce a torque in the first rotational direction R1 to the plunger 40.

During assembly of the drive subassembly 10.1 the plunger 40 with the drive spring 30 is inserted into the proximal region 21. Once the plunger 40 reaches a proximal position the first plunger boss 40.1 is axially aligned with the profiled slot 21.1. By rotating the plunger 40 in a second rotational direction R2 by an angle, e.g. approximately 30°, the first plunger boss 40.1 is moved into the profiled slot 21.1. In this position the first angled surface 21.2 moves the first plunger boss 40.1 against the wall 21.3 by inducing a torque to the plunger 40 in the first rotational direction R1 due to the drive spring 30 biasing the plunger 40 in the distal direction D.

In order to assemble the drug delivery device 10, a syringe 24 may be inserted into the control subassembly which may comprise the distal region 20 of the housing 11.

Afterwards, the drive subassembly 10.1 is inserted into the control subassembly in the distal direction D. The proximal region 21 and the distal region 20 may comprise snap connections to lock them together when assembled. During the final assembly of the drug delivery device 10 the sleeve 13 may be partially depressed to allow initiation of the plunger release mechanism 25, e.g. by an assembly jig (not illustrated) or in a different way.

Figure 6:
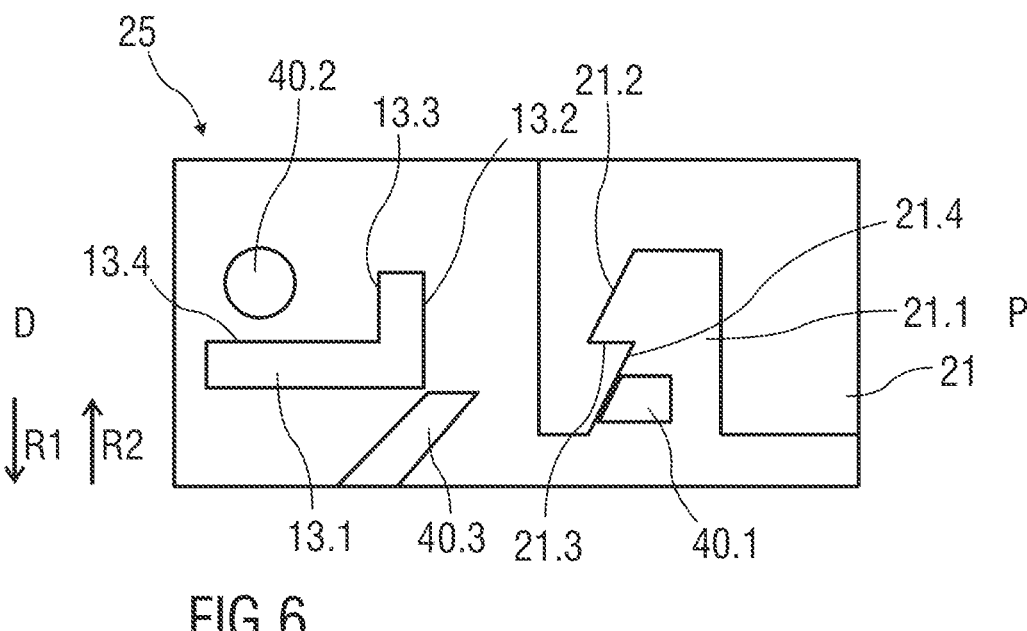
FIG. 6 is a schematic view of the plunger release mechanism during final assembly.
Figure 7:
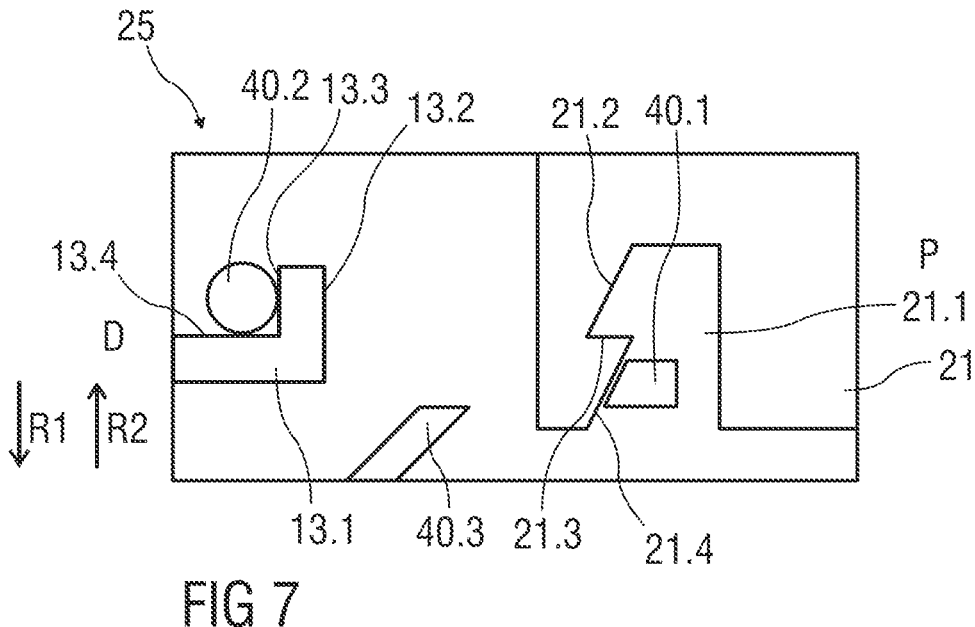
FIG. 7 is a schematic view of the plunger release mechanism after final assembly.

FIG. 6 shows the plunger release mechanism 25 during the final assembly. The sleeve rib 13.1 proximally abuts the angled plunger rib 40.3 thereby inducing a torque to the plunger 40 in the first rotational direction R1 and pushing the plunger 40 in the proximal direction P so that the first plunger boss 40.1 moves along the wall 21.3 until it disengages from the wall 21.3. Due to the induced torque, the first plunger boss 40.1 moves in the first rotational direction R1 and engages the second angled surface 21.4. The depression of the sleeve 13 may cease and, due to the first plunger boss 40.1 engaging the second angled surface 21.4 and the drive spring 30 acting on the plunger 40 in the distal direction D, the plunger 40 rotates further in the first rotational direction R1. As the sleeve 13 is not being depressed further it may move in the distal direction D relative to the housing 11, e.g. under the action of a sleeve spring (not illustrated). This movement is limited by the second plunger boss 40.2 abutting the distal face 13.3 on the sleeve rib 13.1. Further rotation of the plunger 40 in the first rotational direction R1 is prevented by the second plunger boss 40.2 abutting the longitudinal face 13.4 of the sleeve rib 13.1. The load of the drive spring 30 is resolved within the proximal region 21 by the first plunger boss 40.1 engaging the profiled slot 21.1. This state of the plunger release mechanism 25 is illustrated in FIG. 7.

A sequence of operation of the drug delivery device 10 may be as follows:

The user removes the cap assembly 12 pulling it in the distal direction D away from the housing 11. Removal of the cap assembly 12 may at the same time remove a protective needle sheath from the needle 17.

The sleeve 13 is in an extended position protruding from the housing 11 in the distal direction D. The extended position may be defined by the second plunger boss 40.2 proximally abutting the distal face 13.3 of the sleeve rib 13.1.

The user may then press the drug delivery device 10 with the sleeve 13 ahead against an injection site, e.g. a patient's skin thereby moving the sleeve 13 from the extended position towards a retracted position against the bias of the shroud spring.

Figure 8:
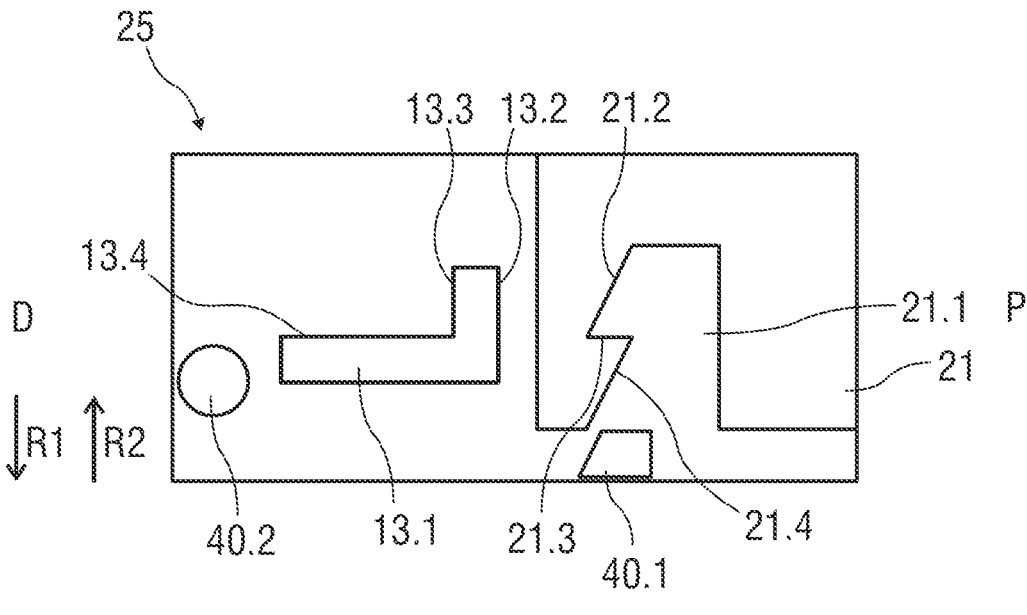
FIG. 8 is a schematic view of the plunger release mechanism after depression of a sleeve.

FIG. 8 is a schematic view of the plunger release mechanism 25 after depression of the sleeve 13 into the retracted position. As the sleeve 13 is being moved from the extended position towards the retracted position the second plunger boss 40.2 moves (starting from the position shown in FIG. 7) relative to the sleeve 13 in the distal direction D guided along the longitudinal face 13.4 of the sleeve rib 13.1.

In an exemplary embodiment the longitudinal face 13.4 of the sleeve rib 13.1 may comprise an interruption or bump feature (not illustrated) for creating an increase in the force required to depress the sleeve 13 further. This may be used to indicate to the user that needle insertion would commence with further depression of the sleeve 13. Up until this point, the user is free to remove the drug delivery device 10 from the injection site and reposition as the sleeve 13 will re-extend to its initial position under the force of the shroud spring.

If the user continues pressing the drug delivery device 10 against the injection site the sleeve 13 is moved into the retracted position exposing the needle 17 and inserting it into the injection site.

Once the sleeve 13 is depressed into the retracted position, and the needle 17 inserted, the second plunger boss 40.2 has moved distally beyond the sleeve rib 13.1 such that the plunger 40 is no longer prevented from rotating in the first rotational direction R1 due to the torque induced by the drive spring 30 and the first plunger boss 40.1 engaging the second angled surface 21.4 on the profiled slot 21.1. The plunger 40 rotates in the first rotational direction R1 due to this torque and the first plunger boss 40.1 comes clear of the profiled slot 21.1. The plunger 40 is thus released and advances the piston 23 in the distal direction D displacing the medicament from the syringe 24 through the needle 17. The release of the first or second plunger boss 40.1, 40.2 may provide audible feedback that delivery of the medicament has started.

Figure 9:
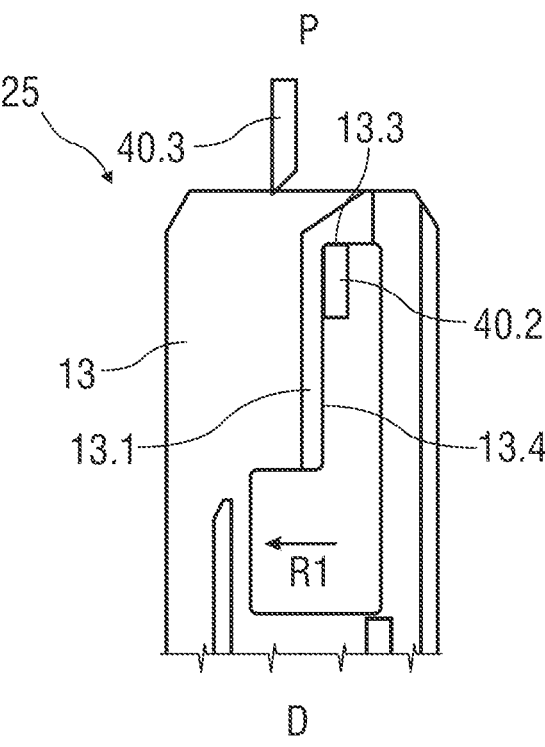
FIG. 9 is a schematic detail view of the plunger release mechanism after final assembly and prior to depression of the sleeve.

FIG. 9 is a schematic detail view of the plunger release mechanism 25 after final assembly and prior to depression of the sleeve 13. Movement of the sleeve 13 in the distal direction D relative to the housing 11 is limited by the second plunger boss 40.2 abutting the distal face 13.3 on the sleeve rib 13.1. Further rotation of the plunger 40 in the first rotational direction R1 is prevented by the second plunger boss 40.2 abutting the longitudinal face 13.4 of the sleeve rib 13.1.

Figure 10:
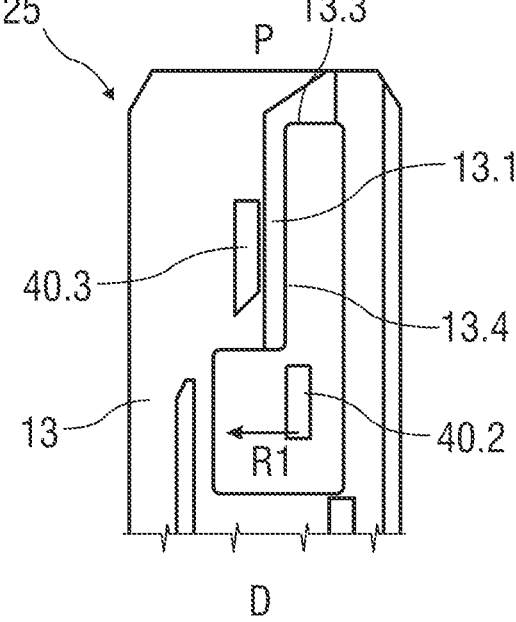
FIG. 10 is a schematic detail view of the plunger release mechanism during depression of the sleeve.

FIG. 10 is a schematic detail view of the plunger release mechanism 25 during depression of the sleeve 13. As the sleeve 13 is being moved from the extended position towards the retracted position in the proximal direction P the second plunger boss 40.2 moves (starting from the position shown in FIG. 9) relative to the sleeve 13 in the distal direction D guided along the longitudinal face 13.4 of the sleeve rib 13.1.

If the user continues pressing the drug delivery device 10 against the injection site the sleeve 13 is moved into the retracted position exposing the needle 17 and inserting it into the injection site.

Once the sleeve 13 is depressed into the retracted position, and the needle 17 inserted, the second plunger boss 40.2 has moved distally beyond the sleeve rib 13.1 such that the plunger 40 is no longer prevented from rotating in the first rotational direction R1 due to the torque induced by the drive spring 30 and the first plunger boss 40.1 engaging the second angled surface 21.4 on the profiled slot 21.1. The plunger 40 rotates in the first rotational direction R1 due to this torque and the first plunger boss 40.1 comes clear of the profiled slot 21.1. The plunger 40 is thus released and advances the piston 23 in the distal direction D displacing the medicament from the syringe 24 through the needle 17.

Figure 11:
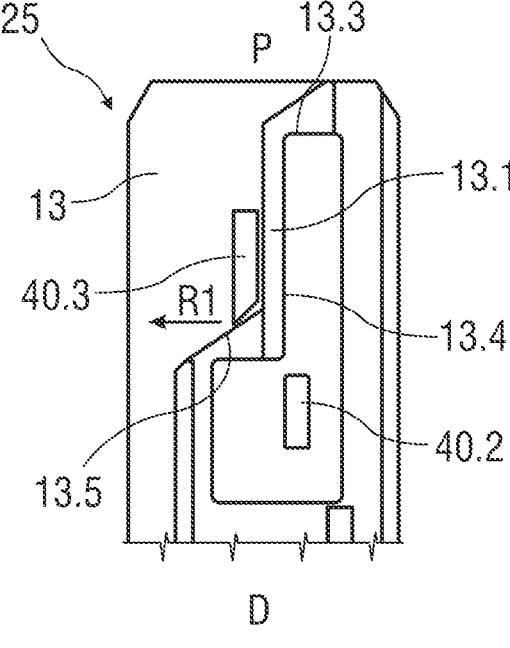
FIG. 11 is a schematic detail view of another embodiment of the plunger release mechanism during depression of the sleeve.

FIG. 11 is a schematic detail view of another embodiment of the plunger release mechanism 25 during depression of the sleeve 13. In addition to the embodiment described above, a sleeve ramp 13.5 is provided on the sleeve 13. As the sleeve 13 approaches the retracted position, the sleeve ramp 13.5 engages a projection such as a rib or boss on the plunger 40, e.g. the angled plunger rib 40.3 to actively rotate the plunger 40 in the first rotational direction R1. If the plunger 40 should not rotate spontaneously due to the features of the previous embodiments, the additional sleeve ramp 13.5 will induce rotation of the plunger 40.

During normal use, the plunger 40 will release as in the previous embodiments. The sleeve ramp 13.5 is positioned to only interact with the angled plunger rib 40.3 if the plunger 40 has not spontaneously rotated near the end of the depression of the sleeve 13. The skilled person will readily understand that the embodiment of FIG. 11 would likewise work if only one of the rib or boss on the plunger 40, e.g. the angled plunger rib 40.3, or the sleeve ramp 13.5 was ramped or angled.

Another benefit of the embodiment of FIG. 11 is that it provides additional guidance of the plunger 40 movement as it activates.

In another exemplary embodiment, the sleeve ramp 13.5 engaging the rib or boss on the plunger 40, e.g. the angled plunger rib 40.3, may be the only way to rotate the plunger 40 out of engagement with the profiled slot 21.1. For example, the profiled slot 21.1 may not have an angled surface causing the plunger 40 to rotate in the first rotational direction R1 out of engagement with the profiled slot 21.1. In an exemplary embodiment, the profiled slot 21.1 may only have a transversal surface towards the distal direction D and transversally oriented relative to the longitudinal axis X. The transversal surface may have a detent or bump. In another exemplary embodiment the profiled slot 21.1 may only have an angled surface causing the plunger to rotate in the second rotational direction R2 maintaining the first plunger boss 40.1 engaged within the profiled slot 21.1.

In an exemplary embodiment, the drug delivery device 10 may be an auto-injector.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about –4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
10.1 drive subassembly
11 housing
11a window
12 cap assembly
13 sleeve
13.1 sleeve rib
13.2 proximal face
13.3 distal face
13.4 longitudinal face
13.5 sleeve ramp
17 needle
20 distal region
21 proximal region
21.1 profiled slot
21.2 first angled surface
21.3 wall
21.4 second angled surface
22 button
23 piston
24 syringe
25 plunger release mechanism
30 drive spring
40 plunger
40.1 first plunger boss
40.2 second plunger boss
40.3 angled plunger rib
D distal end, distal direction
P proximal end, proximal direction
R1 first rotational direction
R2 second rotational direction
X longitudinal axis

The invention claimed is:

1. An assembly for a drug delivery device comprising:
a plunger configured to displace a piston of the drug delivery device, having arranged on the plunger
a plunger boss; and
a plunger holder, wherein the plunger holder comprises
a profiled slot, wherein the profiled slot is adapted to be directly engaged by the plunger boss to inhibit movement of the plunger relative to the plunger holder in a distal direction, and wherein the profiled slot is adapted to induce a rotation to the plunger when an axial force is applied to the plunger, in order to rotate the plunger relative to the plunger holder in a rotational direction, wherein the profiled slot comprises
an angled surface, wherein the angled surface is adapted to engage the plunger boss to induce the rotation; and
wherein the plunger boss is axially and/or rotationally fixed relative to the plunger.

2. The assembly according to claim 1, wherein the plunger boss comprises an angled plunger boss surface, adapted to engage the angled surface, and wherein the angled plunger boss surface is adapted to induce the rotation, when engaged to the angled surface.

3. The assembly according to claim 1, wherein the plunger boss comprises several straight side faces.

4. The assembly according to claim 1, wherein the profiled slot comprises a wall adapted to limit movement of the plunger boss in the rotational direction when engaged to the angled surface, or
wherein the plunger boss comprises two plunger boss side surfaces, and wherein the plunger boss side surfaces extend in the distal direction and are oriented parallel.

5. The assembly according to claim 1, wherein the angled surface is a first angled surface, wherein the profiled slot comprises a second angled surface adapted to engage the plunger boss to induce the rotation to disengage the plunger boss from the profiled slot to allow movement of the plunger in the rotational direction and the distal direction.

6. The assembly according to claim 5, wherein the plunger boss comprises an angled plunger boss surface, wherein the angled plunger boss surface is adapted to engage the second angled surface to induce the rotation to disengage the plunger boss from the profiled slot to allow movement of the plunger in the rotational and distal directions.

7. The assembly according to claim 5, wherein the profiled slot comprises a wall adapted to limit movement of the plunger boss in the rotational direction when engaged to the first angled surface, and wherein the first angled surface is adjacent to the second angled surface and the wall is arranged between the first and second angled surfaces such that the wall separates the first angled surface from the second angled surface.

8. The assembly according to claim 7, wherein the rotational direction is a first rotational direction, and wherein the wall is adapted to allow movement of the plunger boss in a second rotational direction, opposite the first rotational direction, when the plunger boss is engaged to the first or second angled surface.

9. The assembly according to claim 7, wherein the first angled surface, the second angled surface and the wall form a sawtooth shape.

10. The assembly according to claim 5, wherein the second angled surface extends further in the distal direction than the first angle surface.

11. The assembly according to claim 5, wherein the plunger boss is a first plunger boss and the plunger comprises a second plunger boss, and wherein the first and second plunger boss have different shapes.

12. The assembly according to claim 11, wherein the assembly comprises a needle sleeve movable mounted relative to the plunger holder along a longitudinal axis, wherein the needle sleeve comprises a sleeve rib on the needle sleeve, and wherein the plunger comprise a plunger rib, wherein the plunger rib is adapted to abut the sleeve rib with the plunger for moving the first plunger boss from the first angled surface of the profiled slot to the second angled surface of the profiled slot.

13. The assembly according to claim 12, wherein the profiled slot comprises a wall adapted to limit movement of the first plunger boss in the rotational direction when engaged to the first angled surface, and wherein the plunger rib is adapted to abut the sleeve rib to induce the rotation of the plunger in the rotational direction and push the plunger in a proximal direction when the first plunger boss is engaged to the first angled surface and to the wall of the profiled slot.

14. The assembly according to claim 12, wherein the sleeve rib comprises a distal face adapted to engage the second plunger boss of the plunger to limit movement of the sleeve rib in the distal direction relative to the plunger, or
wherein the sleeve rib has a longitudinal face adapted to engage the second plunger boss preventing rotation of the plunger in the rotational direction to keep the first plunger boss engaged to the second angled surface.

15. The assembly according to claim 14, wherein the sleeve rib is adapted to disengage the second plunger boss from the longitudinal face when the sleeve rib is moved in a proximal direction thereby allowing the plunger to rotate in the rotational direction and the first plunger boss to disengage the second angled surface.

16. The assembly according to claim 1, wherein the assembly comprises a drive spring, and wherein the drive spring is arranged within the plunger holder and adapted to bias the plunger in the distal direction, and wherein the plunger is hollow and the drive spring is arranged within the plunger.

17. The assembly according to claim 1, wherein the plunger boss is an integral part of the plunger.

18. A drug delivery device comprising:
the assembly according to claim 1;
a medicament container, wherein the medicament container contains a medicament; and
a housing, wherein the housing houses the medicament container and the assembly.

19. The drug delivery device according to claim 18, wherein the drug delivery device is an auto-injector.

\* \* \* \* \*